(12) United States Patent
Peterson et al.

(10) Patent No.: US 7,862,592 B2
(45) Date of Patent: Jan. 4, 2011

(54) METHODS AND APPARATUS FOR TREATING SPINAL STENOSIS

(75) Inventors: Mark Peterson, Central Point, OR (US); Jonathan Spangler, San Diego, CA (US)

(73) Assignee: NuVasive, Inc., San Diego, CA (US)

( * ) Notice: Subject to any disclaimer, the term of this patent is extended or adjusted under 35 U.S.C. 154(b) by 861 days.

(21) Appl. No.: 11/635,698

(22) Filed: Dec. 6, 2006

(65) Prior Publication Data

US 2007/0162005 A1    Jul. 12, 2007

Related U.S. Application Data

(60) Provisional application No. 60/748,107, filed on Dec. 6, 2005.

(51) Int. Cl.
   *A61B 17/70* (2006.01)
(52) U.S. Cl. ........................ 606/249; 606/279
(58) Field of Classification Search ................ 606/151, 606/246–249; 623/17.11–17.16
See application file for complete search history.

(56) References Cited

U.S. PATENT DOCUMENTS

| | | | |
|---|---|---|---|
| 5,011,484 A | 4/1991 | Breard | |
| 5,496,318 A | 3/1996 | Howland et al. | |
| 5,609,634 A * | 3/1997 | Voydeville | 623/13.11 |
| 5,645,599 A | 7/1997 | Samani | |
| 5,836,948 A | 11/1998 | Zucherman et al. | |
| 6,558,387 B2 | 5/2003 | Errico et al. | |
| 6,626,944 B1 | 9/2003 | Taylor | |
| 6,761,720 B1 | 7/2004 | Senegas | |
| 7,052,497 B2 | 5/2006 | Sherman et al. | |
| 2001/0012966 A1* | 8/2001 | Studer et al. | 623/17.16 |
| 2001/0020188 A1 | 9/2001 | Sander | |
| 2001/0021850 A1* | 9/2001 | Zucherman et al. | 606/61 |
| 2003/0045935 A1* | 3/2003 | Angelucci et al. | 623/17.11 |
| 2005/0165398 A1* | 7/2005 | Reiley | 606/61 |
| 2006/0106381 A1* | 5/2006 | Ferree et al. | 606/61 |
| 2006/0136060 A1 | 6/2006 | Taylor | |
| 2006/0235532 A1 | 10/2006 | Meunier et al. | |
| 2006/0241614 A1 | 10/2006 | Morrison et al. | |
| 2006/0247634 A1* | 11/2006 | Warner et al. | 606/61 |
| 2006/0293662 A1 | 12/2006 | Boyer, II et al. | |
| 2007/0093823 A1 | 4/2007 | Booth et al. | |
| 2007/0093825 A1 | 4/2007 | Ferree et al. | |
| 2007/0233096 A1 | 10/2007 | Garcia-Bengochea | |
| 2008/0027438 A1 | 1/2008 | Abdou | |
| 2008/0033552 A1 | 2/2008 | Lee et al. | |

FOREIGN PATENT DOCUMENTS

| | | |
|---|---|---|
| WO | 2006/086241 A2 | 8/2006 |
| WO | 2007/087535 A2 | 8/2007 |

\* cited by examiner

*Primary Examiner*—Eduardo C Robert
*Assistant Examiner*—Steven J Cotroneo
(74) *Attorney, Agent, or Firm*—Jay B. Bell

(57) ABSTRACT

This invention relates generally to spine surgery and, in particular, to methods and apparatus for treating spinal stenosis.

24 Claims, 10 Drawing Sheets

METHODS AND APPARATUS FOR TREATING SPINAL STENOSIS

CROSS REFERENCES TO RELATED APPLICATIONS

The present application is a nonprovisional patent application claiming benefit under 35 U.S.C. §119(e) from U.S. Provisional Application Ser. No. 60/748,107, filed on Dec. 6, 2005, the entire contents of which are hereby expressly incorporated by reference into this disclosure as if set forth fully herein.

BACKGROUND OF THE INVENTION

I. Field of the Invention

This invention relates generally to spine surgery and, in particular, to methods and apparatus for treating spinal stenosis.

II. Discussion of the Prior Art

Spinal stenosis is a narrowing of spaces in the spine which results in pressure on the spinal cord and/or nerve roots. This disorder usually involves the narrowing of one or more of the following: (1) the canal in the center of the vertebral column through which the spinal cord and nerve roots run, (2) the canals at the base or roots of nerves branching out from the spinal cord, or (3) the openings between vertebrae through which nerves leave the spine and go to other parts of the body.

Pressure on the lower part of the spinal cord, or on nerve roots branching out from that area, may give rise to pain or numbness in the legs. Pressure on the upper part of the spinal cord (neck area) may produce similar symptoms in the shoulders, or even the legs. The condition generally occurs in patients who are in their last decade or decades of life.

Laminectomy, which involves removing bone, the lamina, from the vertebrae, is the most common surgical treatment for spinal stenosis. Laminectomy enlarges the spinal canal, thus relieving the pressure on compressed nerves. Surgical burs, drills, punches, and chisels are used during the procedure.

Surgeons risk injuring the nerves or the spinal cord as they enlarge the spinal canal. In addition, elderly patients frequently have co-morbidities that increase the risk of laminectomy. Complications of laminectomy include increased back pain, infection, nerve injury, blood clots, paralysis, prolonged recovery, and death.

Lumbar fusion is frequently preformed in conjunction with laminectomy. Current fusion techniques require abrasion of large surfaces of bone. Bone bleeds during and after abrasion. Current fusion techniques increase the risk of spinal stenosis procedures. Fusion also prolongs patient recovery following spinal stenosis surgery. Furthermore, various fusion techniques require the severing and/or removal of certain soft tissue surrounding the spine, including but not limited to the supraspinous ligament, the intraspinous ligament, the ligamentum flavum, the posterior longitudinal ligament, and/or the anterior longitudinal ligament.

Increasingly, surgeons are looking for improved methods of effecting less invasive treatments for spinal stenosis. The device must be able to be safely and consistently implanted without excess damage to the patient. The present invention is directed at overcoming, or at least improving upon, the disadvantages of the prior art.

SUMMARY OF THE INVENTION

This invention is directed to a surgical apparatus for treating spinal stenosis without the need for a laminectomy. Broadly, the invention resides in an apparatus configured for placement in an intraspinous space, (e.g. posteriorly to a spinal canal between a first spinous process and an adjacent second spinous process). In the preferred embodiment, the device permits spinal flexion while limiting spinal extension, thereby providing an effective treatment for treating spinal stenosis. The invention may be used in the cervical, thoracic, or lumbar spine.

The preferred embodiments teach a spinal apparatus configured for placement between adjacent vertebrae and adapted to fuse to a first spinous process. Various mechanisms, including shape, porosity, tethers, and bone-growth promoting substances may be used to enhance fusion. The tether may be a wire, cable, suture, allograft tissue, or other single or multi-filament member. Preferably, the device forms a pseudo-joint in conjunction with the non-fused vertebra.

The spinous process spacer of the present invention may be of bone or non-bone construction. In the bone embodiments, the spinous process spacer may be constructed from any suitable allograft, including but not limited to portions of clavicle, rib, humerus, radius, ulna, metacarpal, phalanx, femur, tibia, fibula, or metatarsal bone. In non-bone embodiments, the spinous process spacer may be any suitable construction, including but not limited to polyaryletherketone (PEEK) and/or polyaryletherketoneketone (PEKK). In either event, the spacer includes a slot or indent to receive a portion of a spinous process to enhance fusion. The device may contain one or more bone-growth promoting substances such as BMP1, 2, 3, 4, 5, 6, 7, 8, 9, 10, 11, 12, 13, 14 . . . n, demineralized bone matrix, allograft cancellous bone, autograft bone, hydroxyapatite, coral and/or other highly porous substance.

During insertion of the spinous process spacer of the present invention, it may become necessary to sever the supraspinous and interspinous ligaments. In such instances it may be desirable to include an overlay designed to extend from one of the first and second spinous processes to the other in order to restore the integrity and functional benefits of the supraspinous and/or intraspinous ligaments.

BRIEF DESCRIPTION OF THE DRAWINGS

Many advantages of the present invention will be apparent to those skilled in the art with a reading of this specification in conjunction with the attached drawings, wherein like reference numerals are applied to like elements and wherein.

DESCRIPTION OF THE PREFERRED EMBODIMENT

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The spinal alignment system disclosed herein boasts a variety of inventive features and components that warrant patent protection, both individually and in combination.

Figure 1:
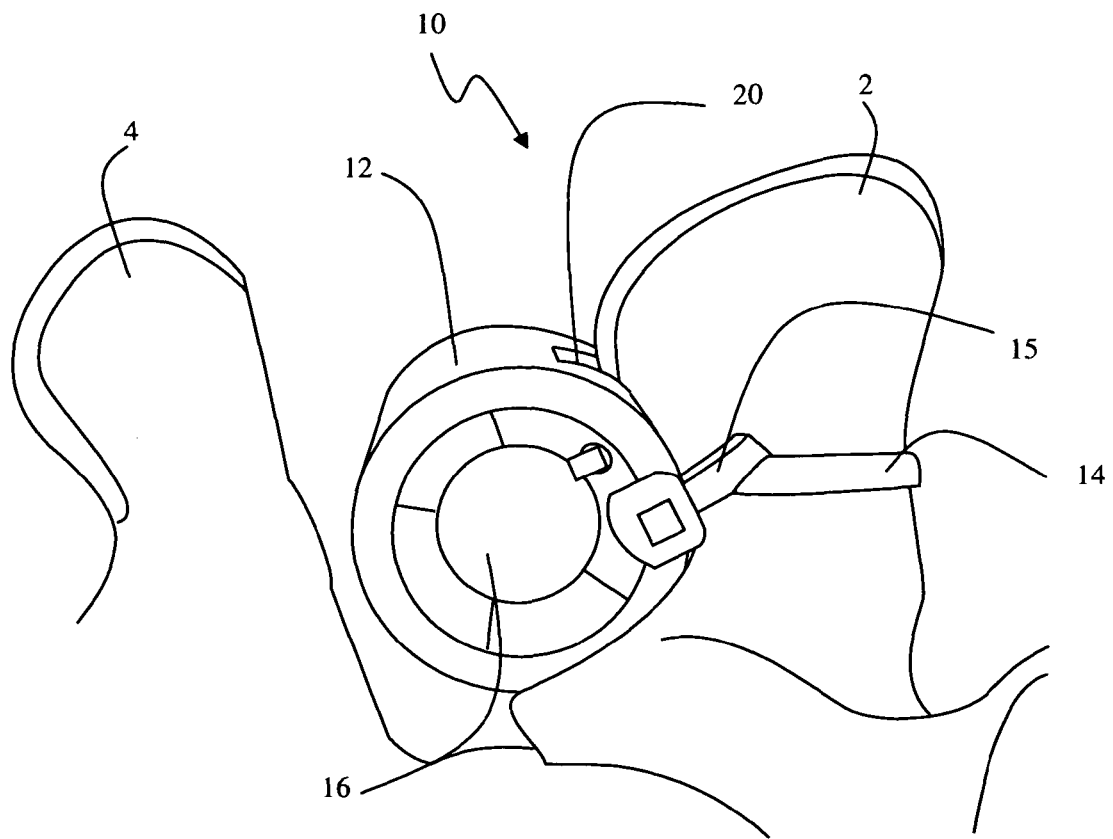
FIG. 1 is a side view of the spinous processes of a pair of adjacent vertebrae with a spinous process spacer according to one embodiment of the present invention inserted therebetween, illustrating in particular the spinous process spacer tethered to one spinous process during use.

FIG. 1 illustrates a perspective view of a spinous process spacer ("SPS") assembly 10 of the present invention in use between the spinous processes of a pair of adjacent vertebrae in a human spine. The SPS assembly 10 includes a spacer 12, a primary tether 14, and two side tethers 15 (only one of which is shown in FIG. 1). The spacer 12, as illustrated in FIGS. 4-8, is generally cylindrical and includes a main chamber 16, a pair of insertion tool apertures 18, a fusion notch 20, and a pair of tether lumens 22. As will be described in greater detail below, according to a preferred embodiment the spacer 12 is coupled to only one spinous process (e.g. the superior spinous process 2 as shown in FIG. 1). This is accomplished, by way of example only, by securing the primary tether 14 to the superior spinous process 2 (as a first step of affixation), and then using a pair of side tethers 15 to affix spacer 12 to the primary tether 14. This step may be accomplished, by way of example only, by passing one side tether 15 through each of the tether lumens 22, further passing the side tether 15 between the superior spinous process 2 and the primary tether 14, and finally tightening each side tether 15 until the spacer 12 is generally transverse to the longitudinal axis of the spine.

Figure 2:
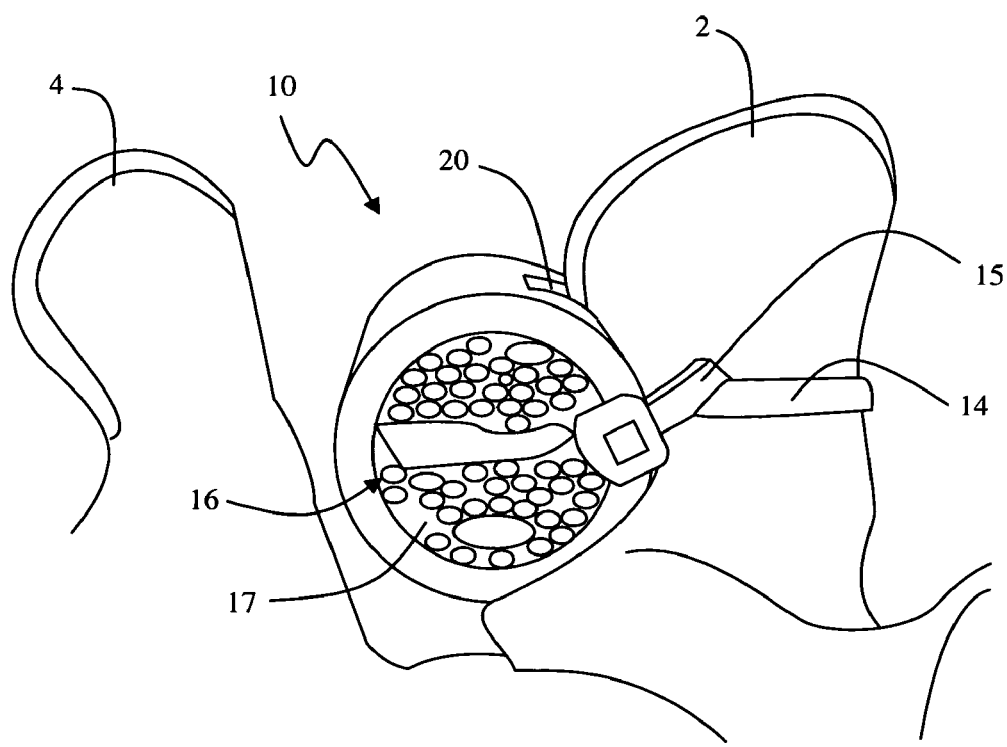
FIG. 2 is a perspective view of the spinal process spacer assembly of FIG. 1 including bone growth promoting material.

The spacer 12 may be of bone or non-bone construction. The bone embodiment involves manufacturing the spacer 12 from a suitable allograft, including but not limited to clavicle, rib, humerus, radius, ulna, metacarpal, phalanx, femur, tibia, fibula, or metatarsal bone. The non-bone embodiment involves manufacturing the spacer 12 from suitable non-bone materials, including but not limited to polyaryletherketone (PEEK) and polyaryletherketoneketone (PEKK). In either event, the spacer 12 is designed to fuse to the superior spinous process 2 over time, resulting in what is called "hemi-fusion" in that the spacer 12 will be fused to only one spinous process. This may be augmented by disposing any number of suitable fusion-inducing materials 17 within the spacer 12 (as shown by way of example only in FIG. 2), including but not limited to BMP1, 2, 3, 4, 5, 6, 7, 8, 9, 10, 11, 12, 13, 14 . . . n, demineralized bone matrix, allograft cancellous bone, autograft bone, hydroxyapatite, coral and/or other highly porous substance.

Although shown and described with regard to the superior spinous process 2, it will be appreciated that the spacer 12 may also be coupled to only the inferior spinous process 4 without departing from the scope of the present invention. The spacer 12, once positioned, serves to distract the interspinous process space, which advantageously restores foraminal height in stenotic patients and may also indirectly decompress the intervertebral space.

Figure 3:
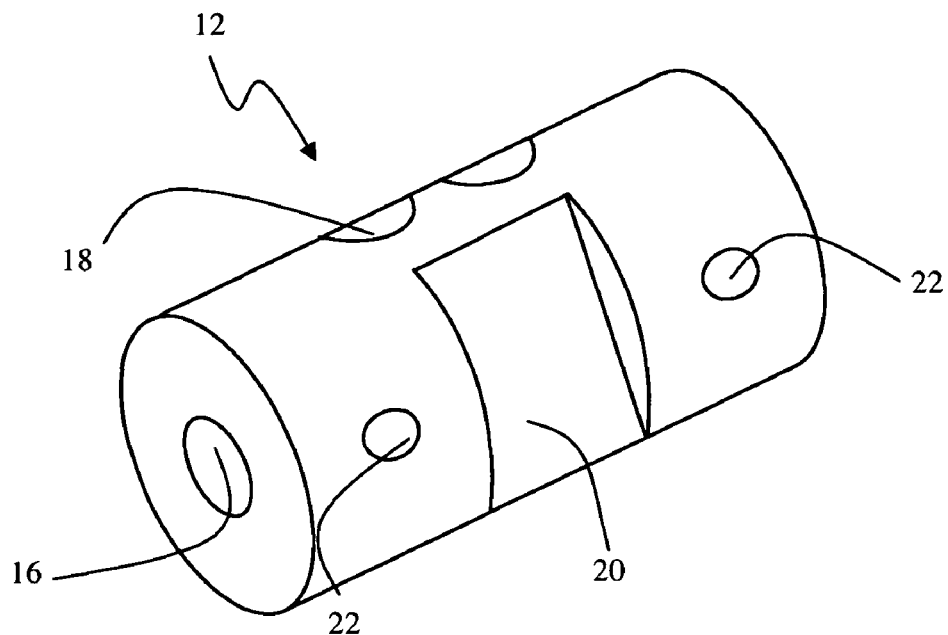
FIG. 3 is a perspective view of a spinous process spacer according to one embodiment of the present invention.
Figure 4:
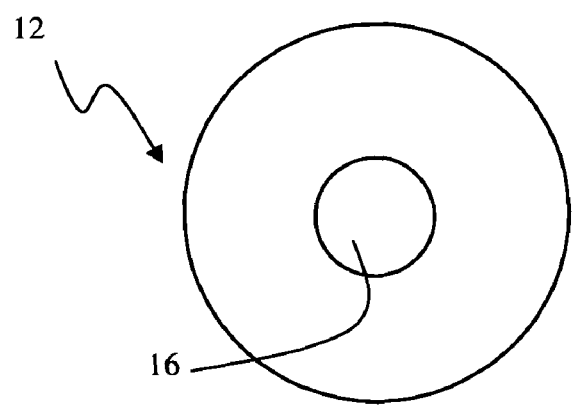
FIG. 4 is a side plan view of the spinous process spacer of FIG. 3.
Figure 5:
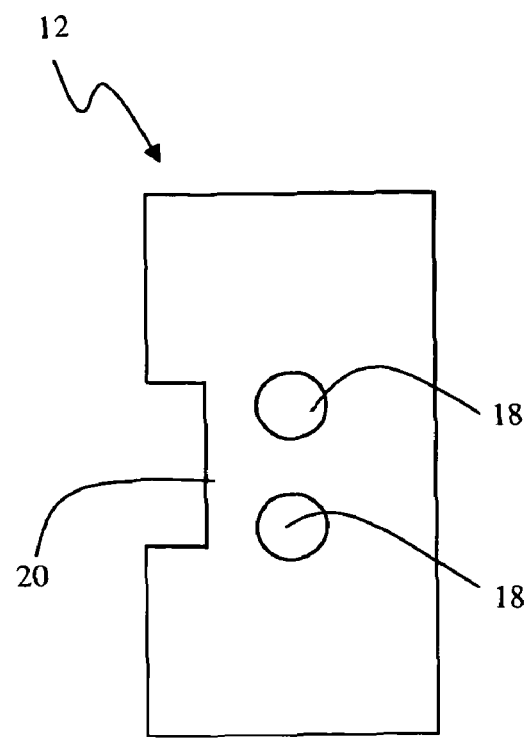
FIG. 5 is a front plan view of the spinous process spacer of FIG. 3.
Figure 6:
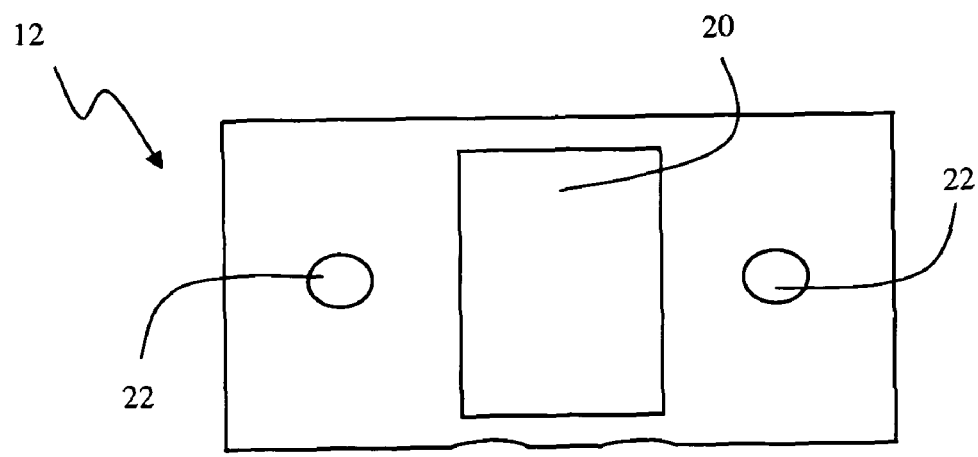
FIG. 6 is a top plan view of the spinous process spacer of FIG. 3.

As depicted in FIGS. 3-4, the main chamber 16 extends through the lateral sides of the spacer 12. The main chamber 16 may be provided in any of a variety of suitable shapes in addition to the generally cylindrical shape as shown, including but not limited to a generally oblong, triangular, rectangular shape and/or combinations thereof. The pair of insertion tool apertures 18 may be located on either the posterior or anterior side of the spacer 12 and extend a portion of the way through the spacer 12. The fusion notch 20 includes a slot or indent to receive a portion of the superior spinous process 2 (or other vertebral structure) to enhance fusion. The fusion notch 20 may be located generally towards the middle portion of the top of the spacer 12. The notch 20 helps center the spacer 12 relative to the superior spinous process.

Figure 7:
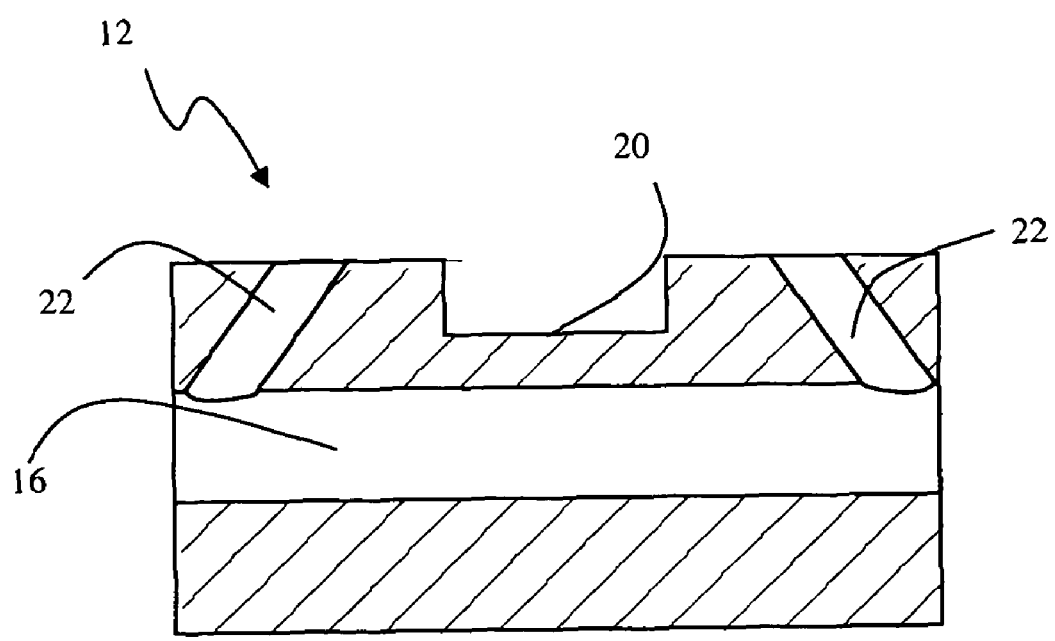
FIG. 7 is a front cross section view of the spacer of FIG. 3.

As best shown in FIG. 7, the tether lumens 22 each extend at an angle through the top surface of the spacer 12 and into the main chamber 16. Each tether lumen 22 may be provided in any of a variety of suitable shapes in addition to the cylindrical shape shown, including but not limited to oblong, triangular, rectangular and/or any combination thereof. The primary tether 14 and the side tethers 15 may comprise any number of suitable materials and configurations, including but not limited to wire, cable, suture thread (permanent and/or bioresorbable), allograft tissue and/or other single or multifilament member. Suture thread may include any number of components capable of attaching to a spinous process, including but not limited to ordinary suture threads known to and used by those skilled in the art of wound closure. The tethers 14, 15 may be of any length necessary to effectively fuse the spacer 12 to the particular spinous process.

Figure 8:
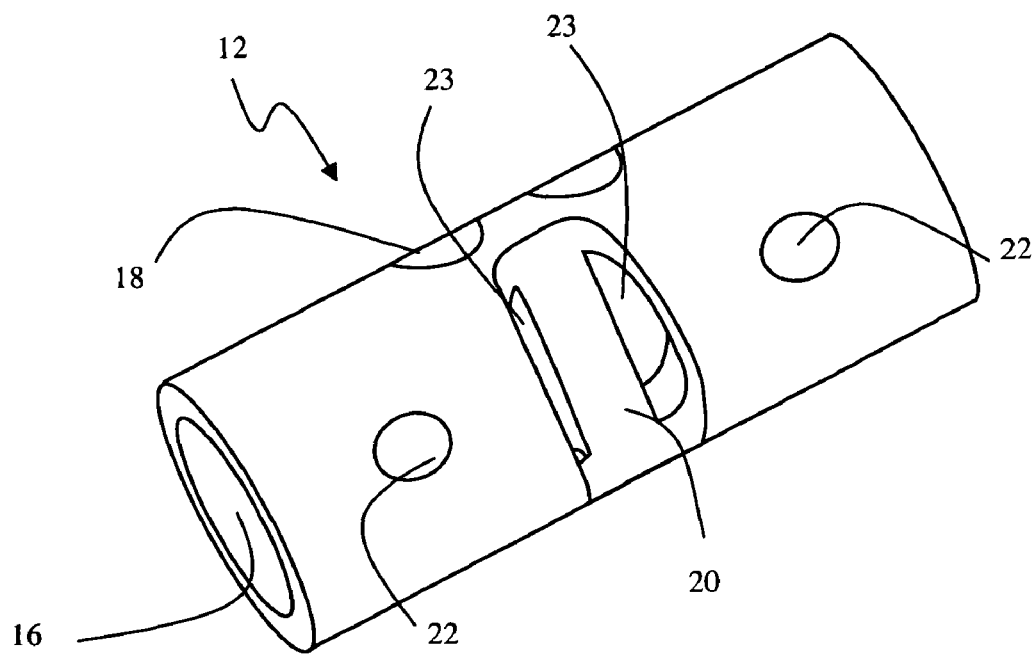
FIG. 8 is a perspective view of a spinous process spacer according to an alternative embodiment of the present invention.
Figure 9:
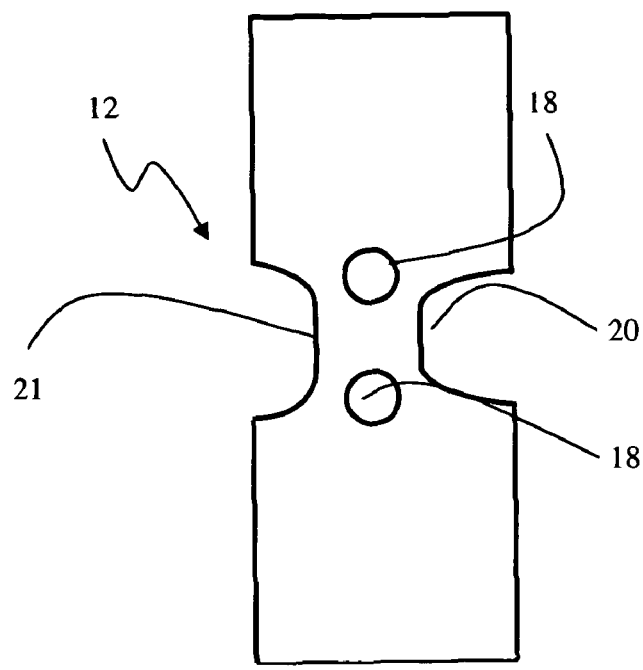
FIG. 9 is a side view of the spinous process spacer of FIG. 8.
Figure 10:
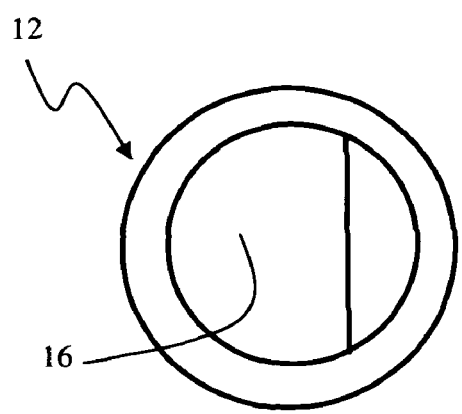
FIG. 10 is an end view of the spinous process spacer of FIG. 8.

According to an alternative embodiment of the present invention shown in FIGS. 8-10, the spacer 12 may be provided with a second notch 21 opposite the fusion notch 20. The second notch 21 is capable of resting on the inferior spinous process 4 during use, which may assist in maintaining the spacer 12 in a fully centered position relative to the inferior spinous process 4. As best shown in FIG. 8, the fusion notch 20 may be further provided with slots 23 extending into the main chamber 16. When the spacer 12 is coupled to the superior spinous process 2, these slots 23 will establish direct communication between the fusion-inducing compounds provided within the main chamber 16 and the lower aspect of the superior spinous process 2, which advantageously augments the ability of the spacer 12 to fuse to the superior spinous process 2 (particularly if the spacer 12 is constructed of non-bone materials).

Figure 11:
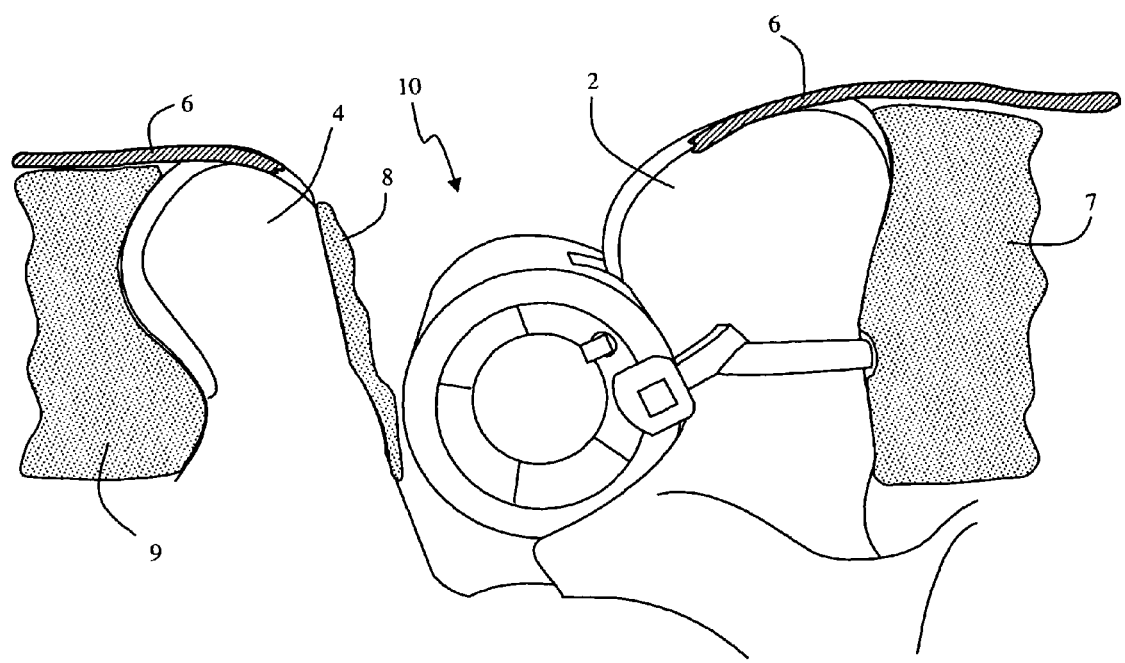
FIG. 11 is a side view of the spinous processes of a pair of adjacent vertebrae with a spinous process spacer according to one embodiment of the present invention inserted therebetween, illustrating the spinous process spacer tethered to one spinous process during use and further illustrating the disruption of the supraspinous ligament and the intraspinous ligament during insertion.

During insertion of the spinous process spacer of the present invention, it may become necessary to sever the supraspinous and interspinous ligaments. FIG. 11 illustrates a SPS assembly 10 attached to a superior spinous process 2 as described above. Supraspinous ligament 6 is illustrated having been severed during the insertion process. Intraspinous ligaments 7, 9 remain intact, while intraspinous ligament 8 (situated between superior spinous process 2 and inferior spinous process 4) is also severed.

Figure 12:
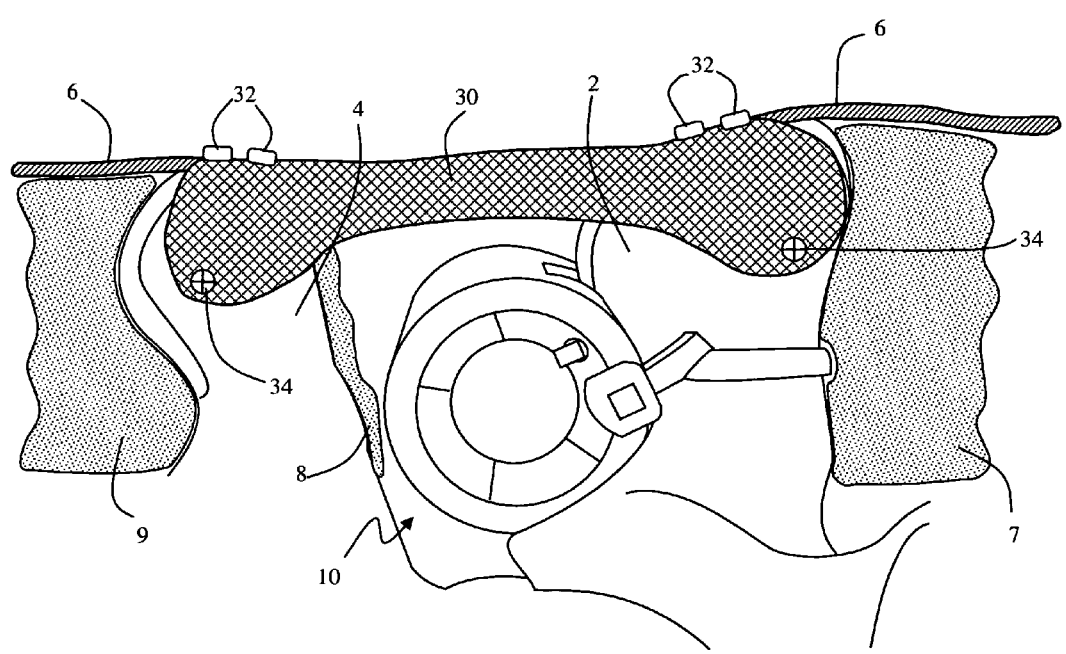
FIG. 12 is a side view of the affixed spinous process spacer of FIG. 11, illustrating the further use of an overlay spanning from one spinous process to the other, primarily covering the distal portions of the spinous processes.

FIG. 12 illustrates an alternative embodiment of the present invention, in which the SPS assembly 10 may further include an overlay 30 designed to extend between the superior and inferior spinous processes 2, 4 in order to restore the integrity and functional benefits of the supraspinous ligament 6. By way of example only, overlay 30 may be any material suitable for restoring the structural and functional integrity of the supraspinous ligament 6, including but not limited to a surgical mesh, textile, and/or embroidery. Exemplary textiles are shown and described in commonly owned U.S. Pat. No. 5,990,378 entitled "Textile Surgical Implants Anchors," which is attached hereto as Exhibit A forming part of this disclosure, and commonly owned US Patent Application Publication No. 2004/0078089 entitled "Textile Prosthesis," which is attached hereto as Exhibit B forming part of this disclosure. Anchors 32 may be used to secure the overlay 30 to the spinous processes 2, 4. Preferably, anchors 32 are inserted into the distal portion of the spinous processes 2, 4, however it is contemplated that anchors 32 may be inserted into any portion of the spinous process suitable to provide purchase. Optionally, side anchors 34 may be inserted into the side of the spinous processes 2, 4 to further secure the overlay 30 to the bone. Anchors 32 and side anchors 34 may be any device suitable for attaching the overlay 30 to the bone, including but not limited to pins, screws, nails, tacks, staples, and the like.

Figure 13:
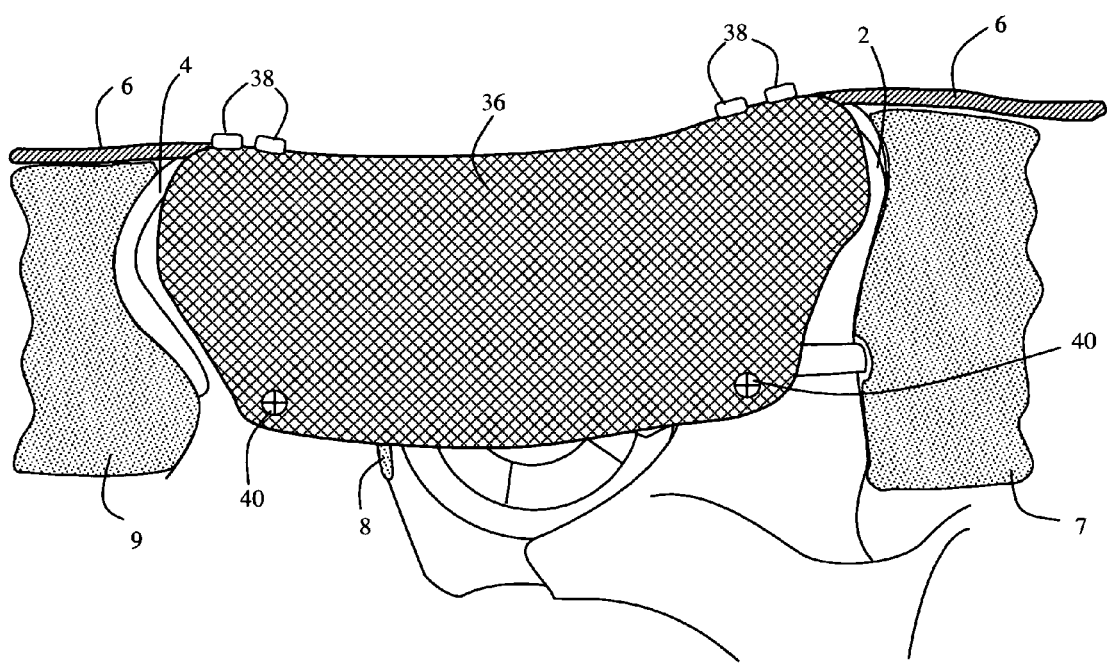
FIG. 13 is a side view of the affixed spinous process spacer of FIG. 11, illustrating the further use of an overlay spanning from one spinous process to the other and covering a significant portion of the spinous processes.

FIG. 13 illustrates a still further alternative embodiment of the present invention, in which the SPS assembly 10 may further include an overlay 36 designed to extend between the superior and inferior spinous processes 2, 4 in order to restore the integrity and functional benefits of the supraspinous ligament 6 and the intraspinous ligament 8. By way of example only, overlay 36 may be any material suitable for restoring the structural and functional integrity of the supraspinous ligament 6, including but not limited to a surgical mesh, textiles, and/or embroidery (including the exemplary textiles referenced above). Anchors 38 may be used to secure the overlay 30 to the spinous processes 2, 4. Preferably, anchors 38 are inserted into the distal portion of the spinous process spacers 2, 4, however it is contemplated that anchors 38 may be inserted into any portion of the spinous process suitable to provide purchase. Optionally, side anchors 40 may be inserted into the side of the spinous processes 2, 4 to further secure the overlay 36 to the bone. Anchors 38 and side anchors 40 may be any device suitable for attaching the overlay 36 to the bone, including but not limited to pins, screws, nails, tacks, staples, and the like.

Although shown as separate components, it is contemplated that overlays 30, 36 may be integrally formed with spacer 12 such that the overlay and spacer are inserted contemporaneously.

The spacer 12 according to the present invention may be constructed of allograft bone and formed in a generally cylindrical shape. The spacer 12 of the present invention may be provided in any number of suitable shapes and sizes depending upon a particular patient and the shape and strength characteristics given the variation from cadaver to cadaver. The spacer 12 may be dimensioned for use in the cervical and/or lumbar spine without departing from the scope of the present invention. The spacer 12 may be dimensioned, by way of example only, having a length ranging between 6-20 mm and a height ranging between 20-25 mm.

The SPS assembly 10 of the present invention may be introduced into a spinal target site through the use of any of a variety of suitable instruments having the capability to releasably engage the spacer 12. In a preferred embodiment, the insertion tool permits quick, direct, accurate placement of the spacer 12 between an upper and lower spinous process. An exemplary insertion tool is shown and described in commonly owned U.S. Pat. No. 6,923,814 entitled "System and Method for Cervical Fusion," which is attached hereto as Exhibit C forming part of this disclosure.

In order to use the SPS assembly 10 of the present invention in a treatment of spinal stenosis, a clinician must first designate the appropriate spacer size 12. A clinician can utilize the SPS assembly 10 in either an open or minimally invasive spinal fusion procedure. In either type of procedure, a working channel would be created in a patient that reaches a targeted spinal level. After the creation of the working channel, the interspinous space would be prepared. After preparation a sizer instrument is used to determine the appropriate size of the spacer 12. Then the spacer 12 is positioned and inserted into the prepared space between the spinous processes. The device forces the spinous processes apart. The spine flexes as the spinous processes are forced apart. The neuroforamina and the spinal canal are enlarged as the spine is flexed. The SPS assembly 10 holds the vertebrae in a flexed position. By way of example only, the SPS assembly 10 may be made from an allograft shaft of a long bone such as the humerus, tibia, fibula, radius, ulna, or femur.

Preparation of the inter spinous process space includes perforating the interspinous ligament between the superior and inferior spinous processes. The supraspinous ligament may be either severed or left intact and distracted out of the way if necessary. A key part of the preparation includes abrading the inferior portion of the superior spinous process where it will communicate with the fusion inducing materials 32 packed in the main chamber 16. Abrading removes the hard cortical bone from the inferior surface of the superior spinous process and leaves bleeding bone which is better adapted for fusion. As new bone generates to heal the abraded portion it may grow into the main chamber 16, fixing spacer 12 to the superior spinous process. In the event that the supraspinous ligament has been severed, it may be desirable to secure an overlay 36 to the superior and inferior spinous processes as described above.

When constructed from allograft, the spacer 12 may be manufactured according to the following exemplary method. If necessary, first use a belt sander to reduce any high spots or imperfections to standardize the shape of the bone. Cut the allograft bone to length using the band saw. Remove the cancellous material from the inner canal to create the main chamber 16. Using calipers, measure the struts and create a size distribution of spacers 12. Machine the insertion tool apertures 18. Set-up a standard vice for holding the implant across its width on the mill. Use a 3⁄32" ball end mill to create the insertion tool apertures 18 (same as cervical allograft implant). Insert the spacer 12 into the vice and tighten. Calculate the centerline of the 20 or 25 mm long spacer 12. Create the holes 2.26 mm away from each side of the centerline (4.52 mm hole to hole distance). Create a notch 22 for the spinous process. Set-up the cervical allograft holding fixture that uses the insertion tool apertures 18 and vice to hold the spacer 12 across its width on the mill. Use a 1⁄4" flat end mill to create the notch 22. Calculate the centerline of the 20 or 25 mm long spacer 12. Insert the spacer 12 onto the fixture using the insertion tool apertures 18 and tighten the vice. This automatically verifies the correct sizing/spacing of the insertion tool apertures 18. Measure the spacer 12 height. Calculate the cut depth to create the desired spacer 12 size. Cut the flat on the spacer 12 to the desired depth. Remeasure the spacer 12 to insure proper cut depth. Drill the angled lumens 22 in face of spacer 12. Remove the spacer 12 from the cervical allograft fixture and tighten into the standard vice. Using a battery powered or corded drill with a 1/16" drill bit, drill through the front face to the canal on both sides. Belt sand the face if needed to create a flat surface for the drill bit to engage the spacer 12.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the invention is to cover all modifications, equivalents, and alternatives falling within the spirit and scope of the invention as defined herein.

What is claimed is:

1. A system for treating spinal stenosis, comprising:
   an implant dimensioned to fit between a superior spinous process and an inferior spinous process, the implant being configured to promote fusion to the superior spinous process, the implant further being configured to discourage fusion to the inferior spinous process, the implant including a first notch dimensioned to receive a portion of the superior spinous process, a second notch positioned on a bottom of the implant dimensioned to engage the inferior spinous process, and at least one aperture positioned within the notch to allow bone to grow into the implant;
   a coupling element configured to couple the implant to the superior spinous process; and
   an overlay dimensioned to extend from at least a portion of the superior spinous process to at least a portion of the inferior spinous process.

2. The system of claim 1, wherein the implant includes an interior chamber in communication with the at least one aperture, the chamber dimensioned to receive fusion inducing material.

3. The system of claim 2, wherein the fusion inducing material includes any of Bone Morphogenic Protein, demineralized bone matrix, allograft cancellous bone, autograft bone, hydroxyapatite and coral.

4. The system of claim 1, wherein the implant includes at least one aperture dimensioned to receive the coupling element.

5. The system of claim 1, wherein the coupling element comprises tether.

6. The system of claim 5, wherein the tether is one of a wire, cable, suture and allograft tissue.

7. The system of claim 1, wherein the implant is made of a non-bone material.

8. The system of claim 7, wherein the implant is made from one of polyetheretherketone and polyetherketoneketone.

9. The system of claim 1, wherein the overlay comprises at least one of surgical mesh, textile and embroidery.

10. The system of claim 1, further comprising a plurality of anchors to secure the overlay to at least one of the superior spinous process and the inferior spinous process.

11. The system of claim 10, wherein the anchors comprise at least one of pins, screws, nails, tacks and staples.

12. The system of claim 1, wherein the overlay is formed as an integral part of the implant.

13. A method for treating spinal stenosis, comprising:
    gaining access to an interspinous process space between a superior spinous process and an inferior spinous process;
    abrading a portion of the superior spinous process;
    inserting an implant in the interspinous process space, the implant being dimensioned to fit between a superior spinous process and an inferior spinous process, the implant being configured to promote fusion to the superior spinous process, the implant further being configured to discourage fusion to the inferior spinous process, the implant including a first notch dimensioned to receive a portion of the superior spinous process, a second notch positioned on a bottom of the implant dimensioned to engage the inferior spinous process, and at least one aperture positioned within the notch to allow bone to grow into the implant;
    coupling the implant to the superior spinous process with a coupling element;
    fitting the portion of the superior spinous process into the notch during insertion; and
    securing an overlay to at least a portion of the superior spinous process and at least a portion of the inferior spinous process such that the overlay extends over the interspinous space.

14. The method of claim 13, wherein the implant includes an interior chamber in communication with the at least one aperture and comprising the additional step of packing the chamber with fusion inducing material one of before and after coupling the implant to the spinous process.

15. The method of claim 14, wherein the fusion inducing material includes any of Bone Morphogenic Protein, demineralized bone matrix, allograft cancellous bone, autograft bone, hydroxyapatite and coral.

16. The method of claim 13, wherein the coupling element comprises a tether.

17. The method of claim 16, wherein the tether is one of a wire, cable, suture and allograft tissue.

18. The method of claim 16, wherein the implant includes at least one aperture dimensioned to receive the tether and comprising the additional steps of:
    introducing the tether through the at least one aperture dimensioned to receive the tether; and
    tying the tether to the superior spinous process.

19. The method of claim 13, wherein the at least one aperture for allowing bone to grow into the implant is positioned within the notch.

20. The method of claim 13, wherein the implant is made of a non-bone material.

21. The method of claim 20, wherein the implant is made from one of polyetheretherketone and polyetherketoneketone.

22. The method of claim 13, wherein the overlay comprises at least one of surgical mesh, textile and embroidery.

23. The method of claim 13, wherein securing the overlay comprises introducing at least one anchor into each of the superior and inferior spinous processes and through said overlay.

24. The method of claim 23, wherein the anchors comprise at least one of pins, screws, nails, tacks and staples.

* * * * *